United States Patent
Scholz et al.

(10) Patent No.: US 8,431,725 B2
(45) Date of Patent: Apr. 30, 2013

(54) PURIFICATION OF LACTIDE RICH STREAMS

(75) Inventors: Reinhard Uwe Scholz, Kerken (DE); Robertus Petrus Maria van der Steen, Vinkel (NL)

(73) Assignee: Niro Process Technology B.V., 'S-Hertogenbosch (NL)

( * ) Notice: Subject to any disclaimer, the term of this patent is extended or adjusted under 35 U.S.C. 154(b) by 619 days.

(21) Appl. No.: 12/531,170

(22) PCT Filed: Aug. 28, 2007

(86) PCT No.: PCT/NL2007/050421
§ 371 (c)(1), (2), (4) Date: Dec. 2, 2009

(87) PCT Pub. No.: WO2007/148975
PCT Pub. Date: Dec. 27, 2007

(65) Prior Publication Data
US 2010/0099893 A1   Apr. 22, 2010

(30) Foreign Application Priority Data

Mar. 14, 2007 (EP) .................. 07104151
May 30, 2007 (EP) .................. 07109223

(51) Int. Cl.
C07D 319/00 (2006.01)
C07D 305/00 (2006.01)

(52) U.S. Cl.
USPC ........................... 549/274; 549/231

(58) Field of Classification Search ................ 549/231, 549/274
See application file for complete search history.

(56) References Cited

U.S. PATENT DOCUMENTS

| | | | |
|---|---|---|---|
| 5,264,592 A | 11/1993 | Fridman | |
| 6,310,218 B1 | 10/2001 | O'Brien | |
| 7,323,016 B2 * | 1/2008 | Heilek et al. | ......... 23/295 R |
| 2003/0175159 A1 | 9/2003 | Heilek | |

FOREIGN PATENT DOCUMENTS

| CN | 1757643 | 4/2006 |
|---|---|---|
| CN | 1757644 | 4/2006 |

OTHER PUBLICATIONS

International Search Report dated Sep. 5, 2008, in PCT application.

* cited by examiner

*Primary Examiner* — Taylor Victor Oh
(74) *Attorney, Agent, or Firm* — Young & Thompson

(57) ABSTRACT

A method for the purification or recovery of lactide rich streams by the combination of a suspension-based melt crystallization process with a subsequent separation of the pure lactide crystals in a wash column is disclosed.

20 Claims, 2 Drawing Sheets

PURIFICATION OF LACTIDE RICH STREAMS

TECHNICAL FIELD

This invention relates to a method for the purification or recovery of lactide rich streams.

BACKGROUND OF THE INVENTION

Lactide is the raw material for the production of biodegradable plastics. High purity lactide is subjected to a ring opening polymerization to form polylactide (PLA). The main use is currently in medical applications, where it applied in three different solid forms, (i) as bone plates and screws for the fixation of fractures or similar purposes, (ii) as solid with tensile strength to produce sutures (stitching material) and (iii) the glue form being used for joining membranes or thins skins in humans. Due to its high strength against UV radiation, it is also used in fibers, as packaging material of e.g. foods and as a solvent. From an environmental protection perspective there is a growing interest for a broader use of PLA in packaging applications since it readily degrades into environmentally acceptable by-products.

Many impurities and specifically hydroxylic impurities like e.g. acids or water have a large chain-stopping potential during polymerization and can thus prevent the attainment of the desired high molecular weights of the PLA. Since the tolerable levels of all impurities in the lactide for the synthesis of PLA are remarkably low, it is therefore economically and ecologically attractive to provide a method that can achieve such required purities in a single and efficient operation.

In addition, the combination of a certain amount of impurities along with high temperature exposure, favors an unwanted early start of the polymerization of the lactide, and results in a decrease of lactide yield and an increase of the product acidity. This is the reason why melt crystallization process are typically preferred against other process operating at higher temperatures: product losses are significant in case of purification by distillation. While the lower operation temperature of the melt crystallization process are preferred as mentioned above, the frequent repetition of multiple batch wise layer melt crystallization steps with the respective melting operations at elevated temperatures can also worsen the lactide yield Lactide exist as an L-isomer, and D-isomer and an M-isomer. While it is typically preferred to use a polymer with a high amount of L-isomer in the production of PLA, a certain racemic mixture of specific isomers would provide different properties of the final polymer; for certain specific applications it may thus be commercially interesting to produce a defined mixture of such isomers.

Known processes for the purification of lactides from the prior art have the disadvantage of being complex, use additional solvents or are inefficient in the sense that their purification potential is limited; typically multiple processes must be executed in series to remove all the impurities. They also generate separate waste streams or use solvents that must be treated and or recovered separately and as a result are prohibitively expensive in terms of process investment and operating cost.

Chinese patent CN 1,757,643 (2006) describes the use of ethyl acetate as solvent for the crystallization of lactides, with the aim to improve the quality of the crystallized product and improve re-crystallization efficiency.

Chinese patent CN 1,757,644 (2006) describes the use of ethanol as solvent for the crystallization of lactides, with the aim to improve the quality of the crystallized product and improve re-crystallization efficiency.

All such methods using a solvent are disadvantageous since they considerably add to the complexity of the process: solvents must be purchased, stored and recovered. Their use must not harm the product in any way and it must not contaminate the environment. Depending on the solvent, their use can also require extensive explosion protection requirements, which additionally adds to the process investment.

U.S. Pat. No. 5,264,592 (1995) describes the use of a melt crystallization process for purification of lactides where the crystals are formed on an interior surface of a crystallizer. With this method the content of the major isomer in the crystallized product is only gradually increased and therefore the frequent repetition of the proposed method is typically compulsory for achieving the required Lactide purities U.S. Pat. No. 6,310,218 B1 (1996) describes the similar melt crystallization process for purification of lactides which—according to the inventors—can only gradually increase the content of the major isomer in the crystallized product and therefore typically requires the frequent repetition of the proposed method to achieve the desired purities.

Discontinuous or semi-continuous static and dynamic layer crystallization processes as described in the above two patents are known from the prior art for other chemical applications: e.g. acrylic acid, DMT, para- and meta-Xylene among others. Such layer melt crystallization processes are characterized by relatively high crystal growth rates between $10^{-5}$ m/s and $10^{-6}$ m/s and result in an impure crystal product. The crystal lattice typically would still remain pure, but the crystals are grown on a cooled surface in a dendrite like structure and mother liquor containing all the impurities gets entrapped into the multifaceted structure. It is known that such dynamic impurity inclusion effects become more pronounced with increasing viscosity. The separation of a single layer melt crystallization process can be enhanced by additional purification methods like sweating and washing: these methods offer an increase in purification efficiency at the expense of the product yield. If such a melt crystallization process is performed in an optimized way by a person skilled in the art, the solid phase can typically be 5 to 10 times purer than the liquid melt, in case additional sweating and/or washing is applied this purification ratio can be as high as 20. In the various examples of U.S. Pat. Nos. 5,264,592 and 6,310,218 B1 above, purification ratios between 2 and 20 are disclosed. Apart from the obvious economical disadvantage of the required process repetitions, such replications lead to a lower process yield and to a higher energy consumption. The lower process yield is due to the fact that only a certain portion can be crystallized out of a certain amount of feed. If, for example 50% of the initial mass is crystallized on the heat exchanger surface of the crystallizer and such process is repeated twice, the final product is only 25% of the initial amount of feed. The various intermediate fraction can also be subjected to the method of the above two inventions thereby increasing the yield again but requiring an even more complex process structure with various purity and various recovery stages. The frequent repetition of multiple batch wise process steps with intermediate melting and re-crystallization consumes much more energy than a single stage process. Due to the much longer processing time along with intermediate periods at higher temperatures, the batchwise layer crystallization process is also subject to ring-opening reactions of the lactic by the presence of impurities and thus characterized by increased lactide losses.

SUMMARY OF THE PRESENT INVENTION

In general terms, the present invention is accordingly based on mitigating or overcoming the disadvantages arising out of the prior art.

In particular, the invention shall make available a method for the ultra-purification or recovery of lactide rich streams which does not use any solvent and which does not require frequent repetition of multiple batch wise process steps.

Furthermore, one of the problems solved by the invention is to make available a method for the ultra-purification or recovery of lactide rich streams, as economically attractive and operationally simple as possible whilst providing high product purity which is required for various applications e.g. in the synthesis of PLA and which will accordingly be highly suitable for large-scale industrial use.

In addition, the invention will make available a method which reduces exposure of the lactide rich feeds to high operating temperatures to the maximum extent possible, thereby minimizing unwanted ring-opening reactions with the lactide and thus maximizing the lactide yield of the method of this invention.

The afore-mentioned problems are solved firstly by the subject matter of the claims herein below. Furthermore, the afore-mentioned problems are solved by a method comprising 1. a continuous efficient suspension based melt crystallization process where the crystals are grown in a carefully undercooled melt in a manner that spontaneous nucleation does not occur and in a way that the crystals (i) do not include any impurities and (ii) are suitable for the subsequent separation in a wash column.
2. separation of the produced lactide crystals in a forced transport type of wash column, which provides a highly efficient countercurrent washing operation without the loss of any wash liquid, wherein such wash liquid comprises the melt of lactide crystals as purified in the said wash column.

Surprisingly it has been found that such method is suitable to produce the required high purity lactide product in a single process while essentially all impurities are discharged in the separated mother liquor.

BRIEF DESCRIPTION OF THE DRAWINGS

The present invention will be described, by way of example, with reference to the accompanying drawings in which.

DETAILED DESCRIPTION OF THE INVENTION

Figure 1:
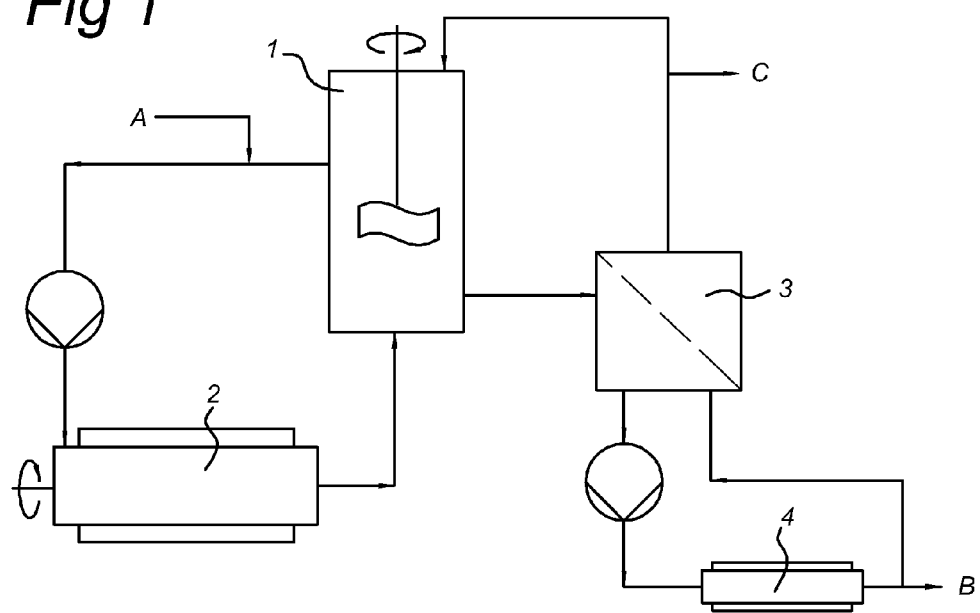
FIG. 1 shows a crystallisation system for carrying out the method of the present invention

In principle the novel method of this invention is suitable for all lactide rich feeds as mentioned in this publication. While this invention is suitable for the purification for the various lactide isomers, the properties of the L-isomer are such that this type is typically preferred in the production of PLA. All concentration figures and temperatures as presented in this invention are given for the purification of a L-lactide rich feed, but may easily be adopted by a person skilled in the art to the respective figures for the other isomers.

Frequently the lactide rich feedstock contains between 80% and 98% of one lactide isomer by weight. Apart from the other lactide isomers the remainder includes, for example, hydroxilic impurities like water, the monomeric lactic acid and other higher boiling oligomers of the lactic acid and other impurities.

The method of the present invention is capable to produce a lactide product with an acceptable purity for the synthesis of polylactide being characterized by a lactide concentration of preferably above 99.5% by weight and more preferably above 99.9% by weight and most preferably above 99.95% by weight, while the level of the residual acidity is preferably below 30 ppm and most preferably below 10 ppm. The water content should preferably be below 400 ppm and more preferably below 100 ppm and most preferably below 50 ppm.

Suspension based crystallization provides a system for continuous operation. While such continuous operation is preferred the process can also be operated batch wise. The large crystal mass of the suspended crystals provides a massive growth surface and allows for very slow and near ideal growth rates. It is preferred that the total available surface area for crystal growth in the suspension process of this method is around some 5,000 to 20,000 $m^2$ per $m^3$ of the crystallizer volume. This far exceeds the growth surface typically available in layer type system which is generally limited to <100 $m^2$ of crystal growth surface per $m^3$ of system volume. The massive growth surface in suspension based crystallization allows that any given undercooling is "absorbed" by such large growth surface and in turn results in extremely slow crystal growth rates in the range of $10^{-10}$ to $10^{-8}$ m/s. At the said slow growth rates the lactide molecules can be included into the highly ordered crystal lattice under equilibrium conditions allowing new lactide molecules sufficient time for the required diffusion from the homogeneously mixed bulk through the boundary layer before they get incorporated into the crystal structure. In layer crystallization the crystal growth rates typically exceeds the diffusion rate of the impurities, which get concentrated in front of the growing crystal layer, back into the bulk solution; such a situation typically leads to a dynamic, non equilibrium controlled inclusion of impurities into the crystal lattice at such faster growth rates: the crystals grow in a dendrite like structure with inclusions of the high purity containing liquid close to the growth surface.

In the preparation of the lactide suspension required according to the invention it is essential that the crystals are grown in the undercooled melt at the said slow growth rates. This can be accomplished in unscraped cooled stirred vessel crystallizers, or in scraped surface crystallizers or in disc crystallizer as described for example in *Melt Crystallization Technology*; G. F. Arkenbout; Technomic Publishing Company Inc.; 1995. The latter two crystallizer have to be operated in a way to constantly sweep the heat exchanger surface in order to slightly undercool the melt, but preventing a crystal layer to develop on the heat exchanger surface. Very generally, all suspension crystallizers which are stated in the above publication as prior art or which are listed in this invention are suitable to be applied for the novel method for the preparation of a lactide suspension.

While the flow of lactide suspension and refrigerant in any suspension crystallizer can be arranged cocurrently or countercurrently, the cocurrent mode of operation is generally preferred.

Suspension crystallization processes, including the crystallization of lactide rich feeds, generally involve both, nucleation and crystal growth. Such two mechanisms are a function of the undercooling as well as other process parameter and system properties and finally determine the crystal size along with its distribution obtained with such crystallization processes. Two different types of nucleation are generally distinguished: primary- or spontaneous nucleation which suddenly starts, when the undercooling exceeds a certain allowed figure and secondary nucleation, which is a function of the undercooling. The inventors found that it is important to avoid spontaneous nucleation at the start of the crystallization process, since this would result in the formation of a viscous inseparable mass of billions of extremely fines crystals suspended in the remaining mother liquor where such tiny crystals cannot be separated from the remaining mother liquor any more. In a specially preferred embodiment of the present invention a seeding procedure is applied in order to start the crystallization process in the absence of spontaneous nucleation, such seeding procedure comprising the steps of:

a) Adding the lactide rich feed solution to a mixing vessel at a concentration such that, when cooled to a temperature between 85° C. and 95° C. said solution will be undercooled with respect to the relevant lactide isomer;
b) Cooling down said lactide rich feed solution to a temperature of preferably between 0° C. and 5° C. and more preferably between 1° C. and 3° C. and most preferably between 1° C. and 2° C. below the freezing point of said lactide rich feed solution
c) Maintaining said lactide rich feed solution at such undercooling and adding seed crystals in an amount to prevent spontaneous nucleation which can turn said lactide rich feed solution into a viscous, inseparable mass of billions of extremely fines crystals suspended in the remaining mother liquor.

In a crystallization process at equilibrium state, the rate of newly formed nuclei has to balance the number of crystals withdrawn from the system. The heat exchanger walls as required for the cooling in suspension based melt crystallization are typically scraped to prevent accumulation of the crystals in a crystal layer at the wall. Although, typical, the inventors were surprised to find that scraping is not a requirement and that the process can be performed with unscraped heat exchangers, as well. In case sufficient mixing is applied, the driving temperature difference between the cooling medium and the lactide suspension for a process without scraped surface heat exchangers has to be limited to a figure of about 5K. In case of insufficient turbulence this driving temperature difference has to be lower. The inventors found that seeding is required to allow for a stable operation of a cooled vessel crystallizer without scraping. The authors believe that an insufficient nucleation rate in the crystallizer under such conditions is the reason for such phenomenon: when the rate at which crystals are withdrawn from the system is larger than the quantity of newly formed nuclei, the number of growing crystals in the vessel will gradually decrease; this in turn will eventually result in a sudden nucleation. While the effect is less pronounced than at the start of crystallization, it leads to a sudden decrease in the crystal size with related problems in the subsequent crystal liquid separation. The authors found that seed crystals in an amount of preferably 0.01 to 2% by weight and more preferably between 0.1 and 1% by weight are advantageously added to the mixing vessel in order to avoid cycling of the crystal size and allow for stable long operation periods. Such seeds can be added continuously or intermittently preferably at intervals between 10 and 30 minutes without any markable influence on the crystal product quality.

While scraping of the heat exchanger surface is not required, it was unexpectedly found that scraping is an efficient means to avoid the continuous or intermittent addition of seed crystals. The combined cooling and scraping action at the crystallizer wall produces sufficient fines as to avoid such addition of seed crystals. Since the production of such seed crystals as well as the continuous or intermittent addition thereof is a complex and costly procedure it is a preferred embodiment of this invention to use a crystallizer with a scraped surface heat exchanger. Such a scraped surface heat exchanger can also be operated at a higher temperature difference between the product suspension and the cooling side, thereby requiring less heat exchanger surface to be installed.

Of course the required amount of energy to be discharged from the system to effect the crystallization can be effected by indirect cooling (e.g. jacketed vessels and heat exchangers), and/or by direct cooling (e.g. use of a coolant with or without phase transition of such coolant.

Very generally, the lactide crystal suspension as produced according to the method of this invention can be separated by any solid-liquid device as known in the prior art. Such solid-liquid device may include, for example, filter, vacuum filter, pressure filter, centrifuges and the like. The large crystal surface area allowing the optimum growth conditions during preparation of the lactide suspension, will negatively affect most attempts at separation. Impurities in the remaining liquid will adhere to all crystal surfaces and gets included into the interstitial spaces of a compacted crystal cake: a highly efficient crystal-liquid separation is therefore required to completely remove these impurities and create a lactide product suitable for synthesis to PLA. Conventional mechanical separations require extensive washing to achieve even moderately pure product. In case molten product is used as washing liquid, about 10% to 20% of the crystallized product is lost and needs to be recycled to the crystallization process. In case a solvent is used as washing agent, such solvent would need to be recovered, which further increases complexity of the whole process.

In a specially preferred embodiment of the present invention the lactide suspension is therefore separated and further purified in wash columns. According to the invention all wash columns which are mentioned in this publication as prior art can be used. The publications *Melt Crystallization—Fundamentals, Equipment and Applications* edited by Joachim Ulrich, Shaker Verlag, 2003 and *Melt Crystallization Technology*; G. F. Arkenbout; Technomic Publishing Company Inc.; 1995 may be mentioned by way of example. Especially wash columns with forced transport as described in patents EP1427502B1, EP0920894B1, EP0097405B1, U.S. Pat. No. 3,872,009 and EP0083463B1 are particularly advantageous according to the invention and are included herein as reference.

The equipment for the method of this invention can be made of all types of plastics or metals or combination thereof, but preferably at least the wash column is made of stainless steel 316 L or 316 Ti.

While tracing is essential to keep all equipment required for performing the method of the present invention free from encrustations and/or blockages, the inventors found that a sophisticated tracing along with a proper control of the tracing temperature around the wash column is crucial for the achievement of the purification results of the present invention. The inventors found that it is particularly useful to apply different tracing temperatures at the unwashed part of the wash column and at the opposite washed part of the wash column.

Of course the novel procedure can also be used a number of times in series. It is particularly advantages to subject the residual mother liquor (C) from the purity crystallizer to a second crystallization step where more lactide crystals are formed and to partially separate these crystals to form a lactide enriched product that is combined with the initial lactide rich starting mixture and a liquid residue that is discharged from the process. In this way the recovery of the total process can be further increased, while potentially maintaining the option to crystallize the lactide product only once. Such a combined process is disclosed in EP1398064 B1, which is included herein by reference.

The invention will now be explained in greater detail herein below with reference to the non-limiting figures:

The suspension based melt crystallization system consists of four main components; (a) mixing vessel to suspend the crystals in mother liquor, (b) heat exchanger to discharge the amount of heat from the process as required for the formation of lacitde crystals. In an preferred embodiment of the present invention said heat exchanger features a scraping device (c) optionally an additional mixing vessel to optimize the mixed crystal flow and (d) a wash column for efficient removal of the crystals from the mother liquor. Components (a) and (b) may be combined into a single apparatus without any detrimental effects to the crystallization process.

Figure 2:
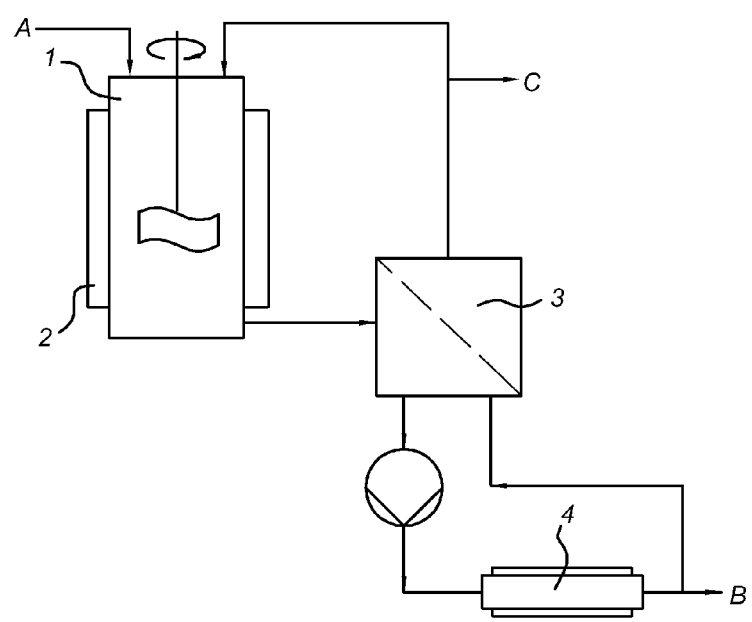
FIG. 2 shows a crystallisation system for carrying out the method of the invention showing a combined heat exchanger and mixing vessel.
Figure 3:
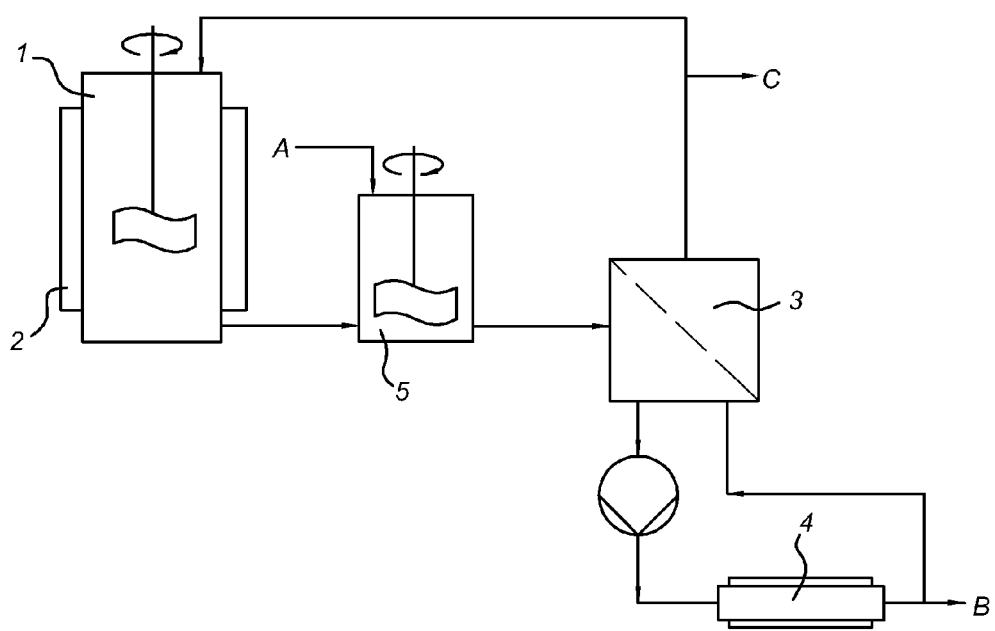
FIG. 3 shows a system for carrying out the method of the present invention comprising an additional mixing vessel upstream of the wash column.

The specific process is described with reference to FIG. 1. FIG. 2 illustrates an equally advantageous configuration where components (a) and (b) are combined. The specific crystallization apparatus is not the intent of the invention and both systems are readily available in industry. FIG. 3 illustrates the process with the additional mixing vessel mentioned in (c) above.

The lactide rich feedstock (A) is fed to and circulated over the scraped surface heat exchanger crystallizer(s) where coolant is preferably circulated in the outer jacket 2.

The scraped surface crystallizer(s) comprises a jacketed vessel containing a rotating scraper assembly to continuously prevent the cooled wall surface of being plugged with a crystal layer. The scraped surface crystallizer(s) are cooled by a secondary heat transfer liquid like e.g. water, brine, ethylene glycol solution or an evaporating refrigerant such as ammonia or Freon® in the outer jacket. Due to the freezing point of lactide rich solutions, water can beneficially be used as cooling agent. The exact configuration is not critical and suitable systems are readily available in industry. The process heat is hereby removed from the system by a cooling system like air coolers in case of a secondary heat transfer liquid or a refrigeration system common in industry. The process equilibrium temperature in the scraped surface crystallizer(s) will typically range from +75° C. to +95° C. and preferably +80° C. to +90° C. The mixing vessel(s) 1 are used to suspend the crystal slurry with typically 15% to 50% lactide crystals by weight and preferably 25 to 35% crystals by weight in the mother liquor.

Surprisingly the intensity of the mixing is not critical and can be maintained at a very low rotational speed of 40 to 100 rpm or just enough to keep the crystal mass from settling to the bottom of the vessel. Again the specific design of the mixing vessel is not the intent of the invention and suitable apparatus are readily available in industry. This amount of crystals provides a massive surface area for crystal growth. High growth surface areas result in very low growth rates. The very slow growth rates provided by suspension based crystallization ensure that the impurities that would normally be included in the rapidly growing crystal surface of a layer crystallization process are now excluded and remain in the mother liquor and results in pure lactide product crystals. The crystal volume in the mixing vessel should be sufficient to provide an average crystal residence time in the range of 15 minutes up to 2 hours and preferably in the range of 30 minutes to 1 hour. Preferably the residence time will not be extended beyond 1 hour since such longer periods will only marginally increase the crystal size. Excessively long residence time increase the complexity and cost of the required equipment. From the mixing vessel(s) the pure crystals suspended in impure mother liquor are fed to one or more wash column(s) 3. The wash column separates the crystals by compressing the slurry and allowing most of the mother liquor to leave through a filter to produce a thickened slurry in the form of a compact crystal bed with between 60% and 90% crystals by weight and preferably 70% to 75% by weight with the remainder being liquid mother liquor containing essentially all of the impurities. The compacted crystal bed is mechanically forced through the column by hydraulic or other mechanical force. The crystal bed is disintegrated and reslurried opposite the original slurry entry point to form a pumpable new slurry in the melter loop (4).

The compact bed is composed of billions of individual crystals and thus forms a porous crystal cake mass within the wash column cylinder. The pressure in the melt loop is controlled by amount of product discharged in stream (B). The pressure in the melt loop 4 is thus controlled to a value higher than in the mixing vessel 1. The open space between the solid lactide crystals is initially filled with impure mother liquor. Due to this pressure difference the melted product is forced counter-current to the crystal flow. The crystals enter the wash column at the same temperature as the crystal slurry typically in the range from +65° C. to +93° C. and preferably +75° C. to +90° C. and most preferably +85 to +90° C. The purified lactide product has melting temperature of +98° C. As the purified lactide product flows thorough the porous crystal bed it will contact the colder crystal and the purified product will re-crystallize onto the surface of the colder crystals. This recrystallization produces new crystalline lactide product form the wash liquid. These new crystals are then carried out with the original crystal mass thus preventing the loss of valuable pure product to the process. The impurities are effectively washed from the surface and totally remain with the mother liquor. The wash column typically uses low pressure steam to melt the crystals in a heat exchanger 4 before discharging the purified product (B).

The results of the application of the invention are described in the examples below in more detail. The various applications of the invention shall, however, not be limited to such working examples, but may be varied with the accompanying claims.

Example 1

An experiment was carried out in a cooled stirred glass beaker crystallizer which was filled with an amount of 500 ml of l-lactide rich feed solution with a concentration of 85 wt. % of l-lactide. The lacitde solution was first cooled to 80° C. and the temperature was then maintained at that level for about 20 minutes. No formation of crystals could be observed. The temperature was then further reduced at a rate of 5° C. per hour and after about 60 minutes and at a temperature of 75° C. spontaneous nucleation occurred, resulting in a viscous inseparable mass of ultra-fine crystals and mother liquor.

Example 2

The first part of the test of example 1 was repeated, but at this time 5 grams of seed crystals with an average length of between 30 m and 150 m were added at a temperature of 80.4° C. Instantly after the addition the temperature in the beaker vessel increased to 83.5° C., indicating the equilibrium temperature of the feed. The temperature in the vessel was then again reduced at a rate of 5° C. per hour and after about 30 minutes the suspension as formed during this experiment was poured into a centrifuge in order to separate off the impurity containing mother liquor. A "dry" filter cake with well defined crystals with a length up to 800 μm was achieved. Contrary to the test in Example 1, these crystals were easy to separate from the slurry.

Example 3

In a dedicated test rig according to FIG. 2 with a scraped surface vessel crystallizer and a mechanical piston column, an impure lactide rich feed was added with a composition as further indicated in table 1.

TABLE 1

Feed composition

| Component: | | |
|---|---|---|
| L-Lactide | wt % | 89.4 |
| M-Lactide | wt % | 2.2 |
| LnA | wt % | 5.0 |
| Other impurities | wt % | 3.4 |
| Residual acidity | meq/kg | |
| water | ppm | |

The scraped surface vessel crystallizer was cooled to a temperature of 85° C. The temperature was maintained at that level and seed crystals were added. Immediately after the seeding the temperature of the crystallizer increased to 86.8° C. By further cooling down the cooling liquid which is circulated through the outer jacket, more crystals were formed. This was evidenced during the test by a continuous further decrease of the temperature in the crystallizer. The constant scraping of the crystallizer walls avoided the formation of any crystals at the heat exchanger surface. Approximately 4 hours after the formation of the first crystals the wash column was started.

The filtered mother liquor from the wash column was initially completely returned to the vessel crystallizer. In this way all impurities in the system kept on accumulating and the concentration of l-lactide decreased continuously. This could be observed by a simultaneous decrease of the temperature in the crystallizer, which represents the equilibrium temperature of the l-lactide solution in the crystallizer at a certain amount of impurities. After an l-lactide concentration of about 80 wt. % was reached a certain amount of reject was discharged from the process to keep the impurity concentration in the process constant. The amount of reject from the process was controlled such as to keep the crystallizer temperature constant. The liquid fraction as rejected from the process via the filter of the wash column had a composition as indicated as example in Table 2

TABLE 2

Reject composition

| Component: | | |
|---|---|---|
| L-Lactide | wt % | 80.0 |
| M-Lactide | wt % | 4.1 |
| LnA | wt % | 9.1 |
| Other impurities | wt % | 6.8 |
| Residual acidity | meq/kg | |
| water | ppm | |

The suspension from the crystallizer was compacted in the wash-column into a dense crystal bed. At the bottom side such packed crystal bed was disintegrated by means of a slowly rotating scraping knife and the individual crystal were re-suspended in re-circulating molten product and then molten in the wash-column melter. A part of this pure product stream was returned into the wash column to achieve the efficient counter-current washing of the crystal bed, while the reminder was discharged from the process as pure product. The wash column purification could be observed visually, indicated by an increasingly clear and white color of the pure product samples compared to the light brownish color of the feed and the reject. As an example for the attained product purities, Table 3 shows a product composition as sampled about 12 hours after the start of the crystallization.

TABLE 3

Product composition

| Component: | | |
|---|---|---|
| L-Lactide | wt % | 99.95 |
| M-Lactide | wt % | 0.05 |
| LnA | wt % | 0 |
| Other impurities | wt % | 0 |
| Residual acidity | meq/kg | 10 |
| Water | ppm | 38.5 |

These results prove that the method of the invention is suitable to produce l-lacitde with the required purity for a further synthesis of polylactide. In particular the produced l-lacitde complied with the pure product specifications for water and acid.

The invention claimed is:

1. A method for the recovery of a lactide containing feed stream in the absence of solvent crystallization, said method comprising the steps of:
   a. Cooling the lactide containing stream to a temperature between 75° C. and 95° C. to form a mixed phase slurry of mother liquor and suspended lactide crystals,
   b. Cooling said slurry to create a volume with a crystal content of between 15% and 50% by weight of the lactide crystals, wherein the crystals are grown in suspension from a slightly under-cooled melt and are not fixed onto an internal crystallizer surface, the available surface for crystal growth being not less than 5,000 $m^2$ per $m^3$ of crystallizer volume, and
   c. Holding said slurry in a mixing vessel to create a crystal residence time between 15 minutes and 2 hours
   d. Separating said crystals from the mother liquid.

2. The method according to claim 1, wherein separation of the crystals from the mother liquid in step (d) is carried out via a wash column.

3. The method according to claim 2, comprising the steps of
   a. Heating a portion of the lactide crystals until they are melted to form a liquid of the purified lactide,
   b. Washing the lactide crystals in the wash column, by contact with the purified melt of said crystals,
   c. Discharging the melted lactide crystals as purified product, and
   d. Discharging impurities in the separated mother liquor.

4. The method according to claim 1 where step a) comprises a seeding procedure, including the steps of:
   a. Adding the lactide containing feed solution to a mixing vessel at a concentration such that, when cooled to a temperature between 80° C. and 96° C. said solution will be undercooled with respect to the relevant lactide isomer;

b. Cooling down said lactide containing feed solution to a temperature of between 0° C. and 10° C. below the freezing point of said lactide containing feed solution, and c. Maintaining said lactide containing feed solution at such under-cooling and adding seed crystals in an amount to prevent spontaneous nucleation.

5. The method according to claim 1, wherein seed crystals in an amount of 0.01 to 2% by weight are added to the mixing vessel.

6. The method according to claim 1, wherein a scraped surface heat exchanger is used for keeping the heat exchanger surface free from incrustations, wherein scraper blades produce such an amount of fines forming seed crystals for preventing spontaneous nucleation.

7. The method according to claim 1, wherein step b) is carried out using separate apparatus for at least one crystal producing step and at least one crystal conditioning step.

8. The method according to claim 1, wherein step b) is carried out using at least one single apparatus for a combined crystal producing—and crystal conditioning step.

9. The method according to claim 7, wherein an additional mixing vessel is used to optimize the mixed crystal flow to the wash column(s) for efficient removal of the lactide crystals from the mother liquor.

10. The method according to claim 2 where step a) comprises a seeding procedure, including the steps of:

a. Adding the lactide containing feed solution to a mixing vessel at a concentration such that, when cooled to a temperature between 80° C. and 96° C. said solution will be undercooled with respect to the relevant lactide isomer;

b. Cooling down said lactide containing feed solution to a temperature of between 0° C. and 10° C. below the freezing point of said lactide containing feed solution, and c. Maintaining said lactide containing feed solution at such under-cooling and adding seed crystals in an amount to prevent spontaneous nucleation.

11. The method according to claim 2, wherein seed crystals in an amount of 0.01 to 2% by weight are added to the mixing vessel.

12. The method according to claim 2, wherein a scraped surface heat exchanger is used for keeping the heat exchanger surface free from incrustations, wherein scraper blades produce such an amount of fines forming seed crystals for preventing spontaneous nucleation.

13. The method according to claim 2, wherein step b) is carried out using separate apparatus for at least one crystal producing step and at least one crystal conditioning step.

14. The method according to claim 2, wherein step b) is carried out using at least one single apparatus for a combined crystal producing—and crystal conditioning step.

15. The method according to claim 8, wherein an additional mixing vessel is used to optimize the mixed crystal flow to the wash column(s) for efficient removal of the lactide crystals from the mother liquor.

16. The method for the recovery of a lactide containing feed stream in the absence of solvent crystallization according to claim 1, wherein the volume of crystal content is between 15% and 50% by weight of the lactide crystals, and the time holding the slurry in the mixing vessel to create the crystal residence is between 30 minutes and 1 hour.

17. The method for the recovery of a lactide containing feed stream in the absence of solvent crystallization according to claim 1, wherein the volume of crystal content is between 25% and 35% by weight of the lactide crystals, and the time holding the slurry in the mixing vessel to create the crystal residence is between 15 minutes and 2 hours.

18. The method for the recovery of a lactide containing feed stream in the absence of solvent crystallization according to claim 1, wherein the volume of crystal content is between 25% and 35% by weight of the lactide crystals, and the time holding the slurry in the mixing vessel to create the crystal residence is between 30 minutes and 1 hour.

19. The method according to claim 4, wherein the temperature for cooling down the lactide containing feed solution is between 1° C. and 5° C. below the freezing point of said lactide containing feed solution.

20. The method according to claim 4, wherein the temperature for cooling down the lactide containing feed solution is between 1° C. and 2° C. below the freezing point of said lactide containing feed solution.

* * * * *

UNITED STATES PATENT AND TRADEMARK OFFICE
CERTIFICATE OF CORRECTION

PATENT NO. : 8,431,725 B2
APPLICATION NO. : 12/531170
DATED : April 30, 2013
INVENTOR(S) : Scholz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 701 days.

Signed and Sealed this
Eighth Day of September, 2015

Michelle K. Lee
*Director of the United States Patent and Trademark Office*